(12) United States Patent
Lambertz

(10) Patent No.: US 11,871,799 B2
(45) Date of Patent: Jan. 16, 2024

(54) COMPRESSION SOCK OR BANDAGE

(71) Applicant: X-Technology Swiss GmbH, Wollerau (CH)

(72) Inventor: Bodo Lambertz, Schwyz (CH)

(73) Assignee: X-Technology Swiss GmbH, Wollerau (CH)

(*) Notice: Subject to any disclaimer, the term of this patent is extended or adjusted under 35 U.S.C. 154(b) by 263 days.

(21) Appl. No.: 17/269,836

(22) PCT Filed: Jul. 31, 2019

(86) PCT No.: PCT/EP2019/070683
§ 371 (c)(1),
(2) Date: Feb. 19, 2021

(87) PCT Pub. No.: WO2020/038694
PCT Pub. Date: Feb. 27, 2020

(65) Prior Publication Data
US 2021/0235775 A1    Aug. 5, 2021

(30) Foreign Application Priority Data

Aug. 22, 2018  (CH) ...................................... 1015/18
Feb. 12, 2019  (CH) ........................................ 167/19

(51) Int. Cl.
*A41B 11/02*   (2006.01)
*A61F 13/08*   (2006.01)

(52) U.S. Cl.
CPC .............. *A41B 11/02* (2013.01); *A61F 13/08* (2013.01)

(58) Field of Classification Search
CPC ....... A41B 11/003; A41B 11/02; A41B 11/14; A61F 13/08; A41D 13/0543; A63B 21/055
(Continued)

(56) References Cited

U.S. PATENT DOCUMENTS 1,845,630 A * 2/1932 Scholl ................. A61F 13/0203
                                                      206/440
4,216,547 A * 8/1980 Picchione ............ A41D 31/185
                                                         2/22
(Continued)

FOREIGN PATENT DOCUMENTS

EP    1323397 A2 *  7/2003   ............. A61F 13/08
EP    1323397 A2    7/2003
(Continued)

OTHER PUBLICATIONS

Machine-generated translation of EP 1,323,397 A2 via Espacenet Patent Translate; Translation obtained on Jan. 6, 2023 (Year: 2023).*
(Continued)

*Primary Examiner* — Jocelyn Bravo
(74) *Attorney, Agent, or Firm* — Paul D. Bianco; Katharine Davis Wong; Fleit Intellectual Property Law

(57) ABSTRACT

A compression sock or bandage made of a base textile includes a tubular leg having a collar, on which compression elements are arranged over the length of the tubular leg, which have a structure, yarn thickness, or yarn material differing from a structure, yarn thickness, or yarn material of the base textile. The compression elements include at least two opposing helices, which extend circumferentially around the tubular leg from the ankle region in the direction of the collar, and which cross at least once and are connected to the base textile in that the knitting pattern or the yarn of the helices is fastened to the base textile to provide stabilizing support. At least one cushion is formed on the base textile on the front side of the compression sock or bandage along a shin region, which protrudes from the collar to the ankle region and at least partially overlaps the crossing helices.

12 Claims, 3 Drawing Sheets

(58) Field of Classification Search
USPC .......................................... 2/239, 240, 241
See application file for complete search history.

(56) References Cited

U.S. PATENT DOCUMENTS

| | | | | |
|---|---|---|---|---|
| 4,862,523 | A * | 9/1989 | Lipov | A41D 31/185 2/409 |
| 5,048,513 | A * | 9/1991 | Reinhardt | A61F 13/08 602/43 |
| 6,189,155 | B1 * | 2/2001 | Boulanger | A41B 11/14 2/409 |
| 6,286,151 | B1 * | 9/2001 | Lambertz | A41D 31/14 2/239 |
| 6,311,334 | B1 * | 11/2001 | Reinhardt | A61F 13/08 2/239 |
| 9,387,125 | B1 | 7/2016 | Duda | |
| 2002/0152773 | A1 * | 10/2002 | Shibata | A41B 11/02 66/69 |
| 2004/0255358 | A1 * | 12/2004 | Ota | A41D 31/18 2/69 |
| 2006/0130217 | A1 * | 6/2006 | Lambertz | A41B 11/02 2/239 |
| 2006/0143801 | A1 * | 7/2006 | Lambertz | D04B 1/26 2/239 |
| 2011/0196416 | A1 | 8/2011 | Lambertz | |
| 2012/0102613 | A1 * | 5/2012 | Loth | A61F 13/08 2/22 |
| 2012/0102625 | A1 | 5/2012 | Klein | |

FOREIGN PATENT DOCUMENTS

| | | |
|---|---|---|
| WO | 2010046130 A1 | 4/2010 |
| WO | 2016157227 A1 | 10/2016 |
| WO | 2018136867 A1 | 7/2018 |

OTHER PUBLICATIONS

International Search Report dated Oct. 23, 2019 for PCT/EP2019/070683 filed Jul. 31, 2019.
Written Opinion for PCT/EP2019/070683 filed Jul. 31, 2019.
International Preliminary Report, dated Feb. 2, 2021, with Written Opinion for PCT/EP2019/070683 filed Jul. 31, 2019 (English translation).

* cited by examiner

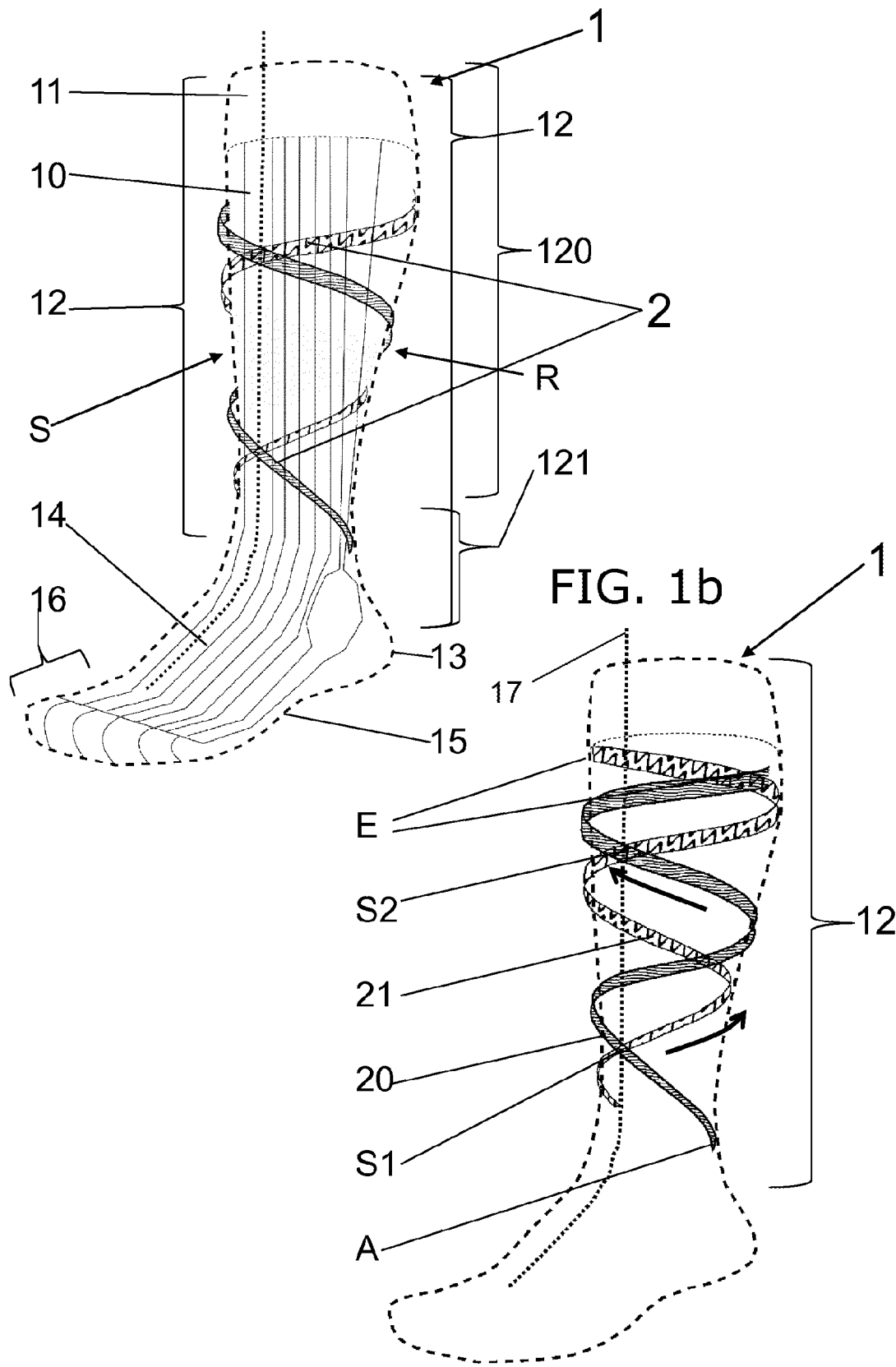

COMPRESSION SOCK OR BANDAGE

BACKGROUND

Field of the Invention

The present invention describes an athletic sock, which is formed from a warp knit or weft knit base textile, has a tubular leg having a collar, wherein compression means are arranged over the course of the leg, which compression means have a structure, yarn thickness, or yarn material different from that of the base textile.

Prior Art

Compression clothing known from the prior art and accordingly also athletic socks and compression stockings generate pressure on the skin and the underlying tissue, in particular an enclosed leg. Compression stockings are used for medical, cosmetic, or prophylactic reasons, for example varicose veins or deep vein thrombosis can be treated or prevented. The risk of a thrombosis, for example on long-haul flights, can be significantly reduced by the prophylactic application. Moreover, compression clothing, in particular compression stockings, are used in sports, for example in Nordic walking or marathon running.

The known compression clothing exerts a planar pressure on the body, in particular in the region of the lower leg. A uniform pressure distribution is achieved by the compression action, which results in a constriction, however, whereby the blood supply is obstructed. This is undesirable above all in the field of sports, so that it has already been known for some time that full-surface compression is unsuitable for use in sports.

Attempts have been made to move away from full-surface compression of the lower leg due to a stocking by arranging multiple stocking regions.

An athletic textile having compression action, in particular an athletic stocking, is known from US 2012102625, wherein at least one compression means is in the form of a band circumferential around the athletic stocking at one height, which is produced from an elastic material in such a way that a local compression effect results.

WO 2018136867 attempted to arrange multiple compression means distributed locally along a weft knit athletic stocking in order to achieve a desired compression effect, whereby the athletic stocking is to be easily producible. Different knitting methods are used and various yarns, wherein components can also be sewn. As is known to a person skilled in the art, ribs or elevations are arranged in the region of the compression means which can bring about a compression effect.

As also described in WO2010046130, it has to be ensured in an optimized athletic textile by suitable arrangement of the compression means that a part of the capillaries are not compressed by webs, elevations, or ribs of the compression means which are formed protruding in the direction of the skin surface. The blood circulation is supposed to remain as undisturbed as possible, so that the cooling of the organism also remains as good as possible, above all during athletic activity. Accordingly, arranging compression means and regions without compression adjacent to one another has become established, which results in sufficient compression effects. However, the resulting compression product is sometimes unsatisfactory, because of which there is a need for development in the design of the compression means. However, it would also be advantageous if annoying muscle vibrations could be remedied in order to increase the stability of the lower leg of a compression stocking wearer or in the region of an elbow or knee joint.

This has been attempted in EP 1323397, in that spiral-shaped circumferential compression means in the form of two opposing helices were used, which are formed circumferentially on the stocking leg from a foot arch region in the direction of a stocking collar. However, the compression thus achievable could not sufficiently reduce or remedy the muscle vibrations in the region of the calf and shin muscles and the ankles. The resulting supporting effect is almost nonexistent with such a solution.

SUMMARY OF THE INVENTION

One aspect of the invention relates to improving an athletic sock or athletic bandage as a compression stocking in such a way that the compression effect is enhanced and additionally a stabilizing supporting effect is achieved in addition at least in the region of a leg and a joint.

For example, the leg muscles are to be fixed and muscle vibrations are to be substantially prevented, whereby the athletic performance is permanently improved.

Accordingly, disclosed is an athletic sock or athletic bandage having a tubular leg, wherein multiple specifically designed compression means are used locally and distributed along the shaft.

Further advantageous embodiments of the athletic sock are explained, in particular on the basis of the example of a compression stocking having compression means, and are claimed in the dependent claims.

An athletic sock or compression stocking or athletic bandage is understood here as a stocking or sock embodied approximately up to the knee of a user, which typically comprises a warp knit or weft knit base textile and is preferably for use in athletic activity and is not used for medical applications.

In addition to the compression means, additional supporting means in the form of cushions are advantageous.

BRIEF DESCRIPTION OF THE DRAWINGS

A preferred exemplary embodiment of the subject matter of the invention is described hereinafter in conjunction with the appended drawings.

FIG. 1a shows a perspective schematic view of an athletic sock, on the basis of the example of a compression stocking having compression means from the front, while FIG. 1b shows a 3D illustration according to FIG. 1a with the focal point of compression means on the front and rear sides and FIGS. 1c to 1g show schematic views of various compression stockings having different numbers of, or differently arranged, compression means.

FIG. 2a shows a view of a compression stocking having compression means and additional cushions in the worn state, drawn over a lower leg, while

DESCRIPTION

Figure 1C:
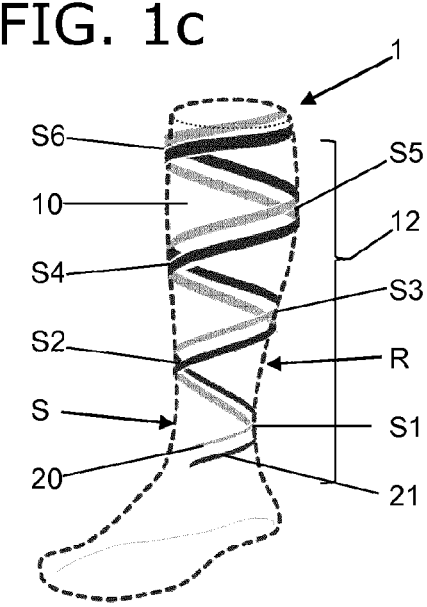

In the following, an athletic sock 1 is described as an example on the basis of the example of an athletic sock 1 or compression stocking 1 made of a base textile, preferably for the use of a user during athletic activity, during which longer stockings or knee stockings are worn.

The compression stocking 1 or the base textile is produced from a warp knit or weft knit textile and comprises here a supporting envelope made of a warp knit base textile 10. From a stocking collar 11, the compression stocking 1 extends in a stocking leg 12, which forms a calf region 120 and an ankle region 121. The calf region 120 and the angle region 121 are each at the height of the corresponding foot regions when the compression stocking 1 of a user is worn. On the side of the stocking leg 12 facing away from the stocking collar 11, a foot arch region 14, a toe region 16, a stocking sole 15, and a heel region 13 adjoin, wherein all compression stocking parts form a compression stocking 1, which encloses a lower leg and is closed toward the stocking sole 15. However, compression stockings 1 which are open on the side opposite to the stocking collar 11 would also be conceivable.

The compression stocking or compression sock 1 is preferably produced in one piece as much as possible from a warp knit base textile 10 on a knitting machine. However, multiple knitted parts can also be produced and subsequently connected to form a compression stocking 1. The schematic view according to FIG. 1a is shown from the direction of a textile front side S, while a textile rear side R is partially concealed. A central extension line 17 of the compression stocking 1 is indicated here by a dashed line, which extends through the middle of the textile front side S from the foot arch region 14 to the stocking collar 11. The stocking collar 11 is typically produced in a knitting pattern and/or yarn differing from the warp base knit textile 10.

The compression stockings described here are advantageously usable in the field of winter sports, sport hunting, or other activities during which longer or knee stockings are advantageous. A compression effect and a muscle-supporting effect are continuously achieved. The stability of the lower leg in the compression stocking 1, and thus the performance of the foot, are improved by the muscle-supporting effect. In spite of the use of such compression means 2, the blood circulation is not disadvantageously changed, since sufficiently many regions of the lower leg are still compressed little or not at all.

Compression means 2 are arranged along the compression stocking 1. These compression means 2 are designed here in the form of multiple opposing helices 20, 21 or spirals, which enclose the stocking leg 12 in a left-handed or right-handed manner. The helices 20, 21 are wound circumferentially around the stocking leg 12 in the direction of the stocking collar 11 at least from the ankle region 120 and cross at least once.

The compression means 2 are preferably formed by at least two helices 20, 21 crossing multiple times having different turn directions, as shown here.

In addition to an increased compression effect, a muscle-supporting or holding effect could also be achieved here. The helices 20, 21 are preferably embodied with warp knit or weft knit textile differing from the warp knit base textile 10 or comprise a different material than the yarn of the warp knit base textile 10.

FIG. 1b shows a compression stocking 1, which comprises along its outer circumference along the stocking leg 12 a first helix 20, which is left-handed here, and a second helix 21, which is embodied right-handed here. The different circumferential directions of the turns are marked by arrows.

Although the stocking leg 12 is not cylindrical, but rather conical, the term helix is used here since the compression means 2 turn like a spiral, curved around the approximately cylindrical stocking leg 12. Each helix 20, 21 starts respectively from a starting point A and encloses the stocking leg 12 here approximately two times until an end point E. Along the helices 20, 21, the turns thus cross twice at a first crossing point S1 and a second crossing point S2. The crossing points S1, S2 are arranged here on the textile front side S and are located along the central extension line of the compression stocking 1. Due to the different turn directions of the helices 20, 21, the two helices also accordingly cross at two crossing points on the textile rear side R.

To achieve a compression, as is known in the field of the compression means on the basis of the warp knit textiles to a person skilled in the art, the helices 20, 21 are defined by different yarns, yarn thicknesses, formed or fastened protrusions, and/or suitable knitting patterns and have a band-like character. The helices 20, 21 are incorporated directly during the production of the compression stocking 1 here into the warp knit base textile 10, for example by a knitting machine.

In modifications, more than two helices 20, 21 can be used, of which only some are opposing and can be arranged offset in the longitudinal direction of the stocking leg 12. Thus, one left-handed and n (n>1) right-handed helices or vice versa could be arranged offset in the longitudinal direction.

In general, the various helices 20, 21 can each originate from the same starting point A and/or end at the same end point E.

It is advantageous if both helices 20, 21 or all helices have more than 1.5 full turns, in particular more than two full turns around the stocking leg 12. The muscle fixing effect is thus enhanced.

The blood flow through the veins back to the heart is assisted and the lower leg muscles are fixed by the helices 20, 21, whereby the stability of the lower leg is enhanced.

The slopes of the helices 20, 21 can be made identical or slightly differing. The pitch height, as the height of a full turn of a helix around the stocking leg 12, can accordingly be designed identically or slightly differing, wherein multiple crossing points of the helices 20, 21 are supposed to occur. If the pitch height corresponds to at least one-fourth of the length between the edge of the stocking collar 11 and the lower edge of the stocking sole 15, an optimum supporting effect can unfold with optimum compression effect simultaneously.

A very good supporting effect is achieved if the at least two helices 20, 21 have more than two crossing points S1 along their courses, wherein the crossing points S1 can be arranged on the textile front side S and/or the textile rear side R.

Since the radius of curvature of the stocking leg 12 is not constant due to the slight conicity of the stocking leg 12, the curvature of the helices 20, 21 is also not constant. During production of a compression stocking on a knitting machine, the selected knitting pattern of the warp knit base textile 10 and the warp knit textile can be adapted accordingly in the region of the helices 20, 21, however.

Figure 1D:
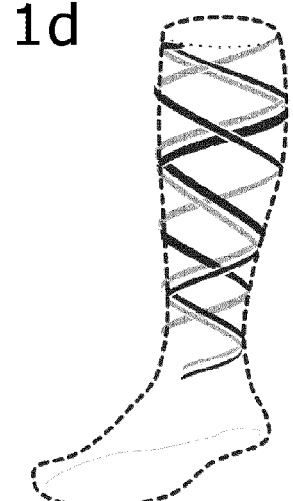
Figure 1E:
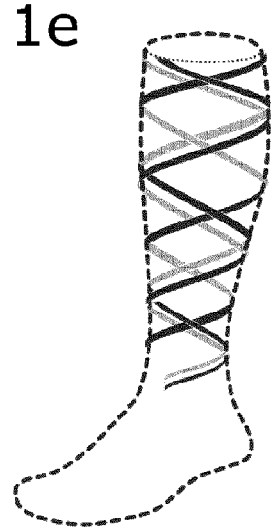
Figure 1F:
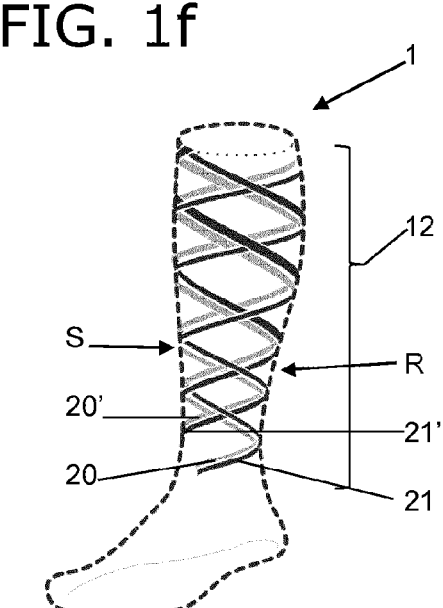
Figure 1G:
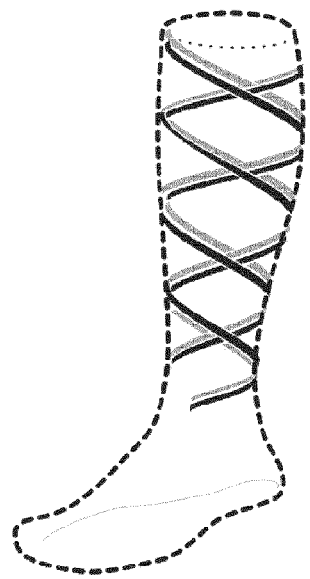

As shown in the compression stockings 1 according to FIGS. 1c to 1g, two helices 20, 21 can be arranged crossing on the textile front side S and the textile rear side R or three helices 20, 20', 21, 21' are selected circumferentially around the shaft 12, as shown in FIGS. 1d and 1e, wherein the helices intersect on the inner side or the outer side of the leg 12. Optionally, four helices can also be selected, of which two pairs each cross, as shown in FIGS. 1f and 1g, wherein crossing points can also be arranged on the textile front side S and/or textile rear side R and/or the leg inner side and/or the leg outer side.

Figure 2A:
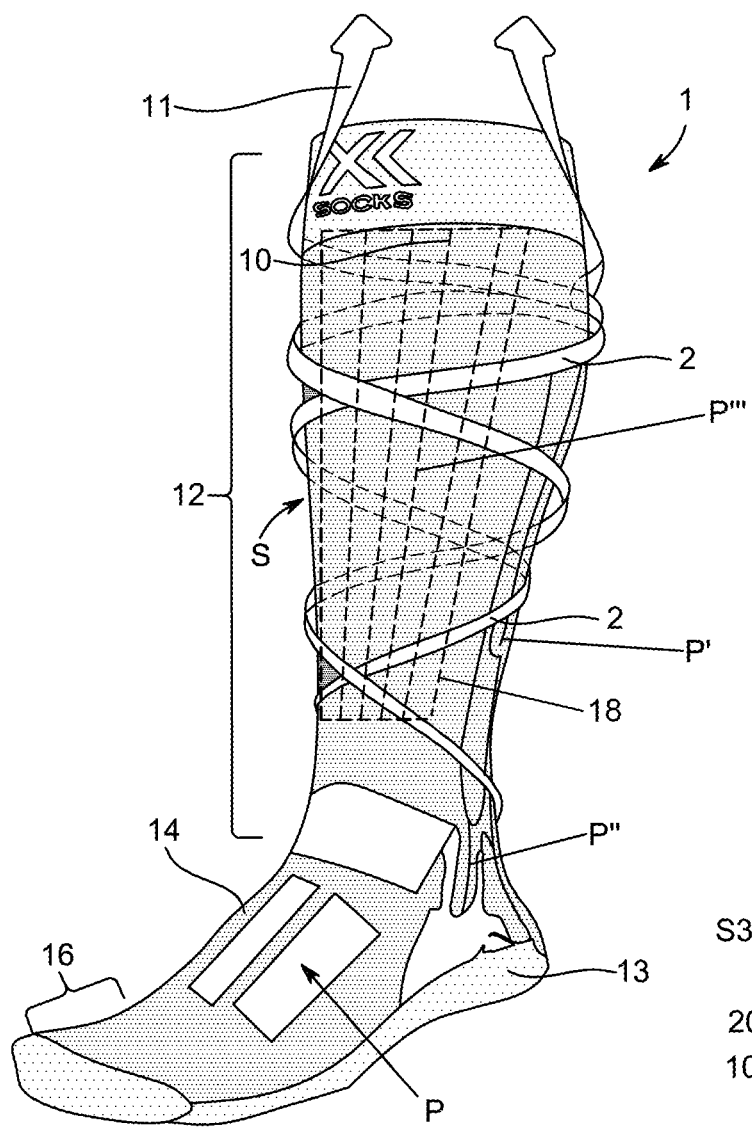

A compression stocking 1 is shown in FIG. 2a, which in addition to the above-described embodiment of circumferential compression means 2, comprises at least one of cushions, P, P', P'', P''', wherein optionally at least one cushion is fastened or formed on the warp knit base textile 10 or is integrated into the warp base textile 10. Two cushions P are attached in the region of the foot arch region 14 of the compression stocking 1 as shown in FIG. 2a. However, cushions P' along the calf region 120, cushions P'' in the ankle region 121, and/or cushions P''' in the region of the shin region 18 are also appropriate for use in the athletic field. A partially planar pressure is additionally generated by cushions P, P', P'', P'''.

The cushion P''' is preferably arranged along a front side of the compression stocking 1, a shin region 18 here, from the stocking collar 11 to the foot arch region 14 protruding on the warp knit base textile 10. The cushion P''' can then overlap the circumferential compression means 2, so that the crossing helices 20, 21 are not recognizable in the shin region 18, since they are covered by the cushion P'''. The compression effect of the helices 20, 21 is also additionally strengthened by the cushion P'''.

Figure 2B:
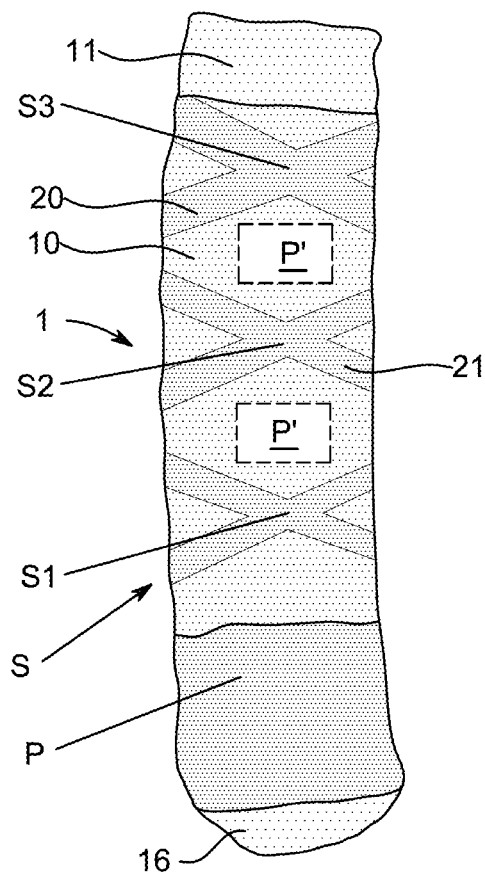
FIG. 2b shows a compression stocking according to FIG. 2a in the flatly designed non-worn state after removal from the warp knitting or weft knitting machine.

In a view according to FIG. 2b of a compression stocking 1 in the folded state, three crossing points S1, S2, S3 are visible on the textile front side S here along the intersecting helices 20, 21. The helices 20, 21 are arranged above the cushion P and the foot arch region 14 extending in the direction of stocking collar 11, wherein the helices 20, 21 do not penetrate into the stocking collar 11. The stocking collar 11 is embodied having a different knitting pattern and/or a different colored yarn than the warp knit base textile 10.

Multiple cushions P' are preferably distributed between the intersecting helices 20, 21 in the calf region 120, i.e., arranged between the crossing points of the helices 20, 21.

The design of the helices 20, 21 is embodied band-shaped here, wherein the thickness varies along the turns. However, it is also possible to embody a constant thickness in the entire turn course. The helices 20, 21 are embodied having a different structure, i.e., preferably having a knitting pattern differing from the warp knit base textile 10. A different yarn, in particular a thicker and/or more flexible yarn, can optionally be selected for the helices 20, 21 than for the warp knit base textile 10. Ribbed structures in the longitudinal direction of the helices 20, 21 or perpendicular thereto can be selected along the helices 20, 21, whereby the compression means 2 can strongly increase the pressure locally on the uppermost skin layer. Since due to the use of warp knit textiles, which generally have a high degree of elasticity, an elastic warp knit base textile and elastic helices 20, 21 are producible, the use of flexible yarn is not absolutely necessary, but is possible. The circumference of the helices 20, 21 can preferably be embodied at the height of the ankle, i.e., enclosing the joint regions 121, of the lower leg of the wearer. An increased support then takes place in the region of the ankle.

Instead of a compression stocking 1, an athletic sock 1 according to the invention having a tubular leg 12 is also used as a bandage for the region of the elbow or knee joints. The leg 12 comprises at least one first side, instead of a stocking sole 15, and a collar 11 on the opposite side. The tubular leg 12 accordingly extends between this first side and the stocking sole 15. The at least two helices 20, 21 are arranged circumferentially around the leg 12 and crossing at least once, wherein the helices 20, 21 are connected to the base textile 10, having a different knitting pattern or different yarn than the base textile 10. The helices 20, 21 are preferably exclusively arranged extending along the length of the athletic sock 1 or the athletic bandage between the foot arch region 14 and a knee region.

The helices 20, 21 have a different knitting pattern and/or different yarn, which are fastened, in particular fastened by knitting, on the base textile 10. The compression means 20, 21 are preferably also warp knitted or weft knitted in during the warp knitting or weft knitting process of the base textile 10, so that the leg 12 forms a closed tubular envelope. If the athletic textile 1 is embodied as a bandage, a first side is then provided opposite to the collar 11 instead of a stocking sole 15. The leg 12 then extends between the first side and the collar 11 and the compression means 2 extend along the leg 12. The cushions P, P', P'', P''' are also knitted into the base textile 10 and are located isolated or congruently adjacent to the helices 20, 21 or overlap them. The cushions P, P', P'', P''' can be produced from thicker yarn, a special knitting pattern, and/or a mixture thereof. The supporting effect of the helices 20, 21 is optimized accordingly by the cushions.

LIST OF REFERENCE SIGNS

1 athletic sock or athletic bandage/compression stocking made of base textile
   10 base textile/warp knit base textile/weft knit base textile (first knitting pattern)
   11 collar/stocking collar, elastically knitted
   12 leg/stocking leg
      120 calf region
      121 joint region/ankle region
   13 heel region
   14 foot arch region
   15 stocking sole
   16 toe region
   17 central extension line
   18 shin region
   S textile front side
   R textile rear side
2 compression means (helices here, at least two helices)
   20, 20' first helix
   21, 21' second helix
   A starting point
   S1, S2, S3, S4, S5, S6 crossing points
   E end point
   P cushion

The invention claimed is:

1. A compression sock or bandage formed from a base textile, the compression sock or bandage comprising:
   a tubular leg extending from a collar at one end to a foot arch region at another end;
   compression elements arranged along a length of the tubular leg, the compression elements having a structure, yarn thickness, or yarn material differing from a structure, yarn thickness, or yarn material of the base textile, the compression elements formed as at least two opposing helices extending circumferentially around the tubular leg from an ankle region in a direction of the collar and crossing at at least one crossing point, each of the at least two opposing helices having a knitting pattern or yarn connected to the base textile; and
   a plurality of cushions distributed along the length of the tubular leg on at least one of a front side of the tubular leg and a rear side of the tubular leg;
   wherein at least one cushion of the plurality of cushions is knitted to the base textile and extends along a surface of the front side of the tubular leg from the collar to the ankle region such that the at least two opposing helices are at least partially covered by the at least one cushion on the front side of the tubular leg.

2. The compression sock or bandage according to claim 1, wherein the base textile is produced from a warp knit or a weft knit.

3. The compression sock or bandage according to claim 1, wherein at least two cushions of the plurality of cushions are arranged on the rear side of the tubular leg between crossing points of the at least two opposing helices.

4. The compression sock or bandage according to claim 1, wherein at least one cushion of the plurality of cushions is arranged on at least one of the foot arch region, a calf region, and the ankle region of the compression sock or bandage.

5. The compression sock or bandage according to claim 1, wherein each cushion of the plurality of cushions has a structure, yarn thickness, or yarn material differing from a structure, yarn thickness, or yarn material of at least one of the base textile and the at least two opposing helices.

6. The compression sock or bandage according to claim 1, wherein the at least two opposing helices begin at a common starting point.

7. The compression sock or bandage according to claim 1, wherein the at least two opposing helices end at a common end point.

8. The compression sock or bandage according to claim 1, wherein the at least two opposing helices have more than three crossing points.

9. The compression sock or bandage according to claim 1, wherein each helix of the at least two opposing helices circumvents the tubular leg for at least two full turns.

10. The compression sock or bandage according to claim 1, wherein each helix of the at least two opposing helices has a pitch height defined by a height of a full turn of the respective helix around the tubular leg.

11. The compression sock or bandage according to claim 10, wherein the at least two opposing helices have different pitch heights.

12. The compression sock or bandage according to claim 10, wherein the pitch height of each helix of the at least two opposing helices corresponds to at least one-fourth of a length between an edge of the collar and a lower edge of the tubular leg or a sole.

* * * * *